United States Patent [19]

Kamada

[11] Patent Number: Plant 5,685

[45] Date of Patent: Mar. 11, 1986

[54] POMEGRANATE TREE

[76] Inventor: Benjamin Y. Kamada, 24627 E. Adams, Orange Cove, Calif. 93646

[21] Appl. No.: 527,085

[22] Filed: Aug. 29, 1983

[51] Int. Cl.[4] ..... A01H 5/03

[52] U.S. Cl. ..... Plt./33

[58] Field of Search ..... Plt./33

*Primary Examiner*—Robert E. Bagwill

*Attorney, Agent, or Firm*—Vergil L. Gerard

[57] ABSTRACT

The present invention related to a pomegranate tree and more particularly to a new and distinct variety thereof broadly characterized by its regular bearing of very early maturing, brightly colored, generally round, pomegranates having a low acidity and being tender with sweetly flavored seed arils and relatively thin rind which resists splitting. The instant pomegranate tree bears the cultivar name Early Red II.

1 Drawing Figure

The present invention relates to a pomegranate tree and more particularly to a new and distinct variety thereof broadly characterized by its regular bearing of very early maturing, brightly colored, generally round, pomegranates having a low acidity and being tender with sweetly flavored seed arils and relatively thin rind which resists splitting.

The instant variety pomegranate tree blooms at the same time as the Early Red (U.S. Plant Pat. No. 2,723) pomegranate tree which the instant variety most nearly resembles. Its fruit, however, distinguishes from the said Early Red variety in that it matures about seven to ten days earlier at which time it has a ratio of acid to the total soluble solids of the fruit which is well below the 1.85% acidity required for harvest. The fruit of the instant variety further distinguishes in some cases from the fruit of said Early Red variety in being slightly smaller in size and having a more uniformly red skin.

I have discovered the instant variety of pomegranate tree as a sport growing on an Early Red pomegranate tree (U.S. Plant Pat. No. 2,723) in an orchard of such trees on my ranch in Fresno County (San Joaquin Valley) Calif. I asexually reproduced it by cuttings made from the original sport. The trees resulting from said cuttings produced fruit and the fruit and tree characteristics proved identical to those of the original sport.

The accompanying drawing is a color photograph of two mature fruit of the instant variety with one divided in a plane taken generally along its major axis to reveal flesh coloration and the edible seed aril thereof.

Referring more specifically to the pomological details of this new and distinct variety of pomegranate tree, the following have been observed under the ecological conditions prevailing at my orchard in Fresno County, Calif., and is an outlined description thereof. All major color plate identifications are by reference to the Nickerson Color Fan of the American Horticultural Council.

TREE

Size: Small, round, compact, and bushy; usually deciduous.

Trunk: Knotty, irregular, suckering freely from roots and crown.

*Branches.*—Slender, twiggy, nearly cylindrical, somewhat thorny; new growth four-angled, with thorns being of modified stem structure and not of leaf origin. Thorns average $\frac{1}{4}''$ to $\frac{3}{4}''$ in length.

Leaves:

*Size.*—Medium.

*Length.*—Averaging 3".

*Width.*—Averaging $\frac{1}{2}''$.

*Form.*—Lanceolate, long or obovate, obtuse, glabrous, red-veined during early growth.

*Color.*—Moderate olive green (5 GY 4/3) to grayish-olive green (5 GY 3/2).

*Margin.*—Without glands and marginal veins.

*Petiole.*—Medium short, medium thick.

*Stipules.*—Few at base of leaf.

Flowers: Profuse, large, axially; solitary or in small clusters; borne mainly at the tips of the branches in the mantle of the tree.

*Size.*—Averaging $1\frac{1}{4}''$.

*Calyx.*—Stiff, tubular, showy; reddish-orange in color, five to seven lobes or sepals, crowned with crumpled petals; bright scarlet and white in color; lanceolate to ovolate in form; equal in number to the sepals and inserted between them.

*Stamens.*—Numerous, inserted on inner wall of calyx tube or receptacle, surmounted by single long, slender style; contains seven to fifteen carpels or locules arranged in two whorls or series, one interior and lower, containing three carpels; the other exterior and upper, containing six to twelve carpels.

*Stigma.*—Small, discoid.

FRUIT

Maturity when described: Firm ripe.

Size: Medium. Axial diameter, averaging $3\frac{1}{4}''$ under normal environmental and horticultural conditions with usual thinning to space fruit along the fruit bearing branches. Transverse in a plane common with the major axis, averaging $3\frac{1}{4}''$. At right angle to major axis, averaging $2\frac{1}{4}''$.

Form: Generally round, obovate, slightly flattened at base and apex.

*Calyx tube.*—Medium to short, lobes reflexed.

*Rind.*—Thin, tough, resists splitting. Color, bright dark red (5R 3/7).

*Flesh.*—Abundant, small amount of rag or pulp; astringent, bitter. Color, brilliant yellow (5Y 9/9).

*Seeds.*—Small in proportion to the aril, fairly tender and easily eaten.

*Aril.*—Succulent, juice abundant, rich flavor, sprightly, vinous and subacid extended to the rind. Color: transparent, dark red (5R 3/4).

Use: Fresh market, local and distant, culinary.

*Keeping quality.*—Excellent.

*Shipping quality.*—Excellent.

Although the new variety of pomegranate tree possesses the described characteristics of the growing condition in Fresno County, Calif., in the central portion of the San Joaquin Valley, it is to be understood that fluctuations of the usual magnitude in characteristics to growing conditions, fertilization, pruning and pest control are to be expected.

Having thus described and illustrated my new variety of pomegranate tree, what is claimed as new and desired to be secured by Letters Patent is:

1. A new and distinct variety of pomegranate tree substantially as illustrated and described which is characterized by its bearing of early maturing fruit which ripens about one week to ten days earlier than the fruit of the patented pomegranate tree U.S. Plant Pat. No. 2,723 commonly known as the Early Red. The new variety most nearly resembles said previously patented pomegranate tree U.S. Plant Pat. No. 2,723 but is distinguished from it by its earlier ripening fruit and in some cases by fruit slightly smaller in size and having a more uniformly red skin.

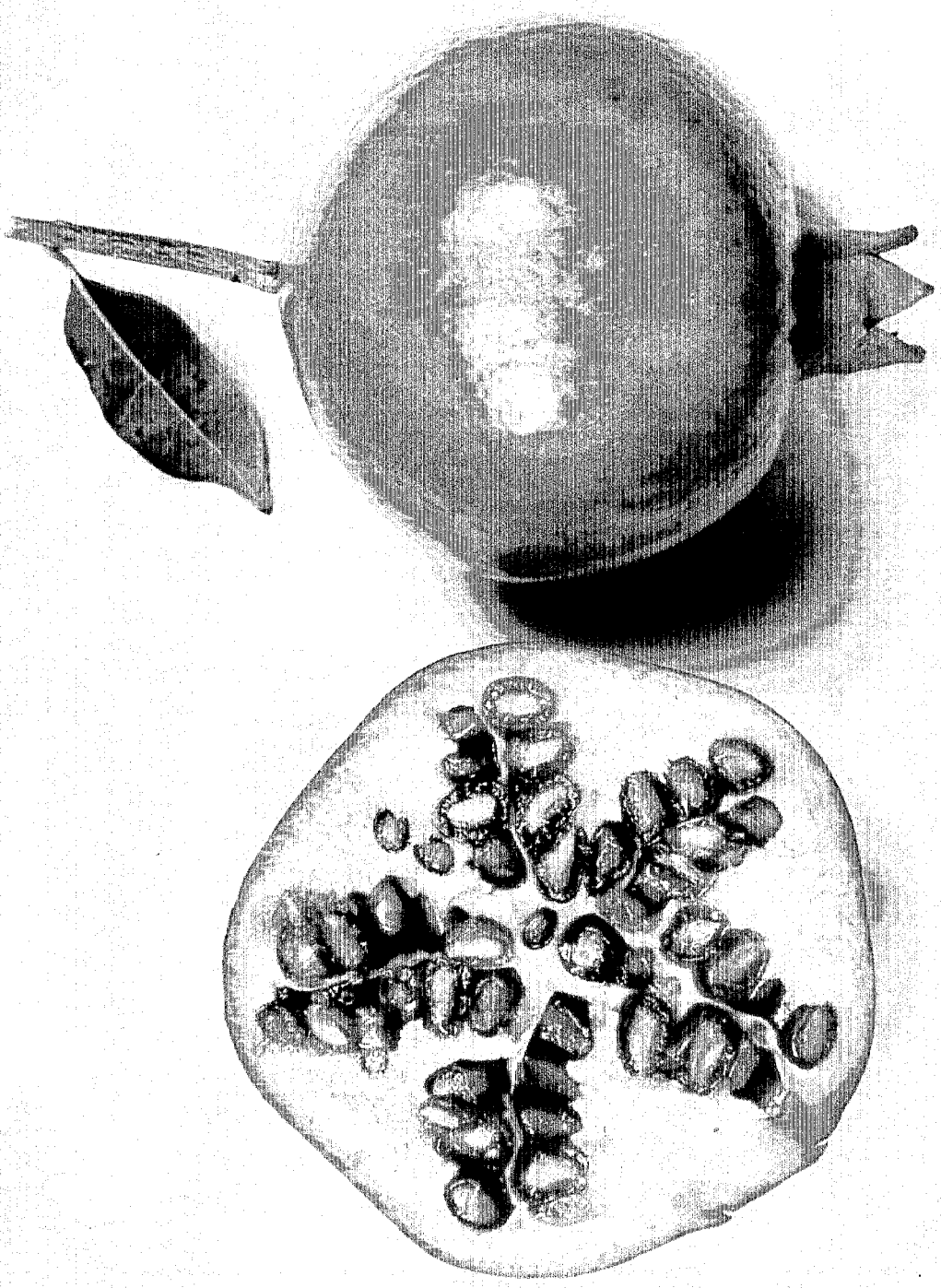

* * * * *